United States Patent [19]

Fung et al.

[11] Patent Number: 5,423,786
[45] Date of Patent: Jun. 13, 1995

[54] STABILIZED ABSORBENT CORE AND PRODUCTS MADE THEREFROM

[75] Inventors: Paul Y. Fung, South River; Robert A. Galloway, Lawrenceville, both of N.J.

[73] Assignee: McNeil-PPC, Inc., Milltown, N.J.

[21] Appl. No.: 126,936

[22] Filed: Sep. 24, 1993

[51] Int. Cl.[6] .................. A61F 13/15; A61F 13/20
[52] U.S. Cl. .................. 604/367; 604/358; 604/359; 604/360; 604/368; 604/372; 604/378; 604/379; 604/380; 604/384; 604/385.1
[58] Field of Search ........ 604/358, 359, 360, 366–368, 604/370, 372–374, 378–382, 384, 385.1

[56] References Cited

U.S. PATENT DOCUMENTS

| | | | |
|---|---|---|---|
| 2,693,439 | 11/1954 | Blanchard et al. | 604/368 |
| 2,952,259 | 9/1960 | Burgent | 604/380 |
| 3,364,931 | 1/1968 | Hirsch . | |
| 3,667,468 | 6/1972 | Nystrand et al. . | |
| 3,699,966 | 10/1972 | Chapuis . | |
| 3,954,107 | 5/1976 | Chesky et al. . | |
| 4,026,291 | 5/1977 | Nagano | 604/368 |
| 4,560,379 | 12/1985 | Stemmler | 604/385.1 |
| 4,576,596 | 3/1986 | Jackson et al. . | |
| 5,330,457 | 7/1994 | Cohen | 604/358 |
| 5,334,177 | 8/1994 | Cohen | 604/358 |

FOREIGN PATENT DOCUMENTS

| | | | |
|---|---|---|---|
| 2124499A | 2/1984 | United Kingdom . | |
| 2255720 | 11/1992 | United Kingdom | 604/378 |

*Primary Examiner*—Randall L. Green
*Assistant Examiner*—P. Zuttarelli

[57] ABSTRACT

An absorbent core for use in an absorbent product suitable for placement in a wearer's garment, and absorbent products utilizing the core, are disclosed. The core comprises an absorbent batt folded upon itself along a pair of generally parallel longitudinal fold lines to form a middle, body-facing panel and two side panels, which three panels are substantially equivalent in width at the central transverse axis of the batt. In various preferred embodiments, one or more of the panels are embossed with patterns that serve to direct fluid transport in the product.

29 Claims, 4 Drawing Sheets

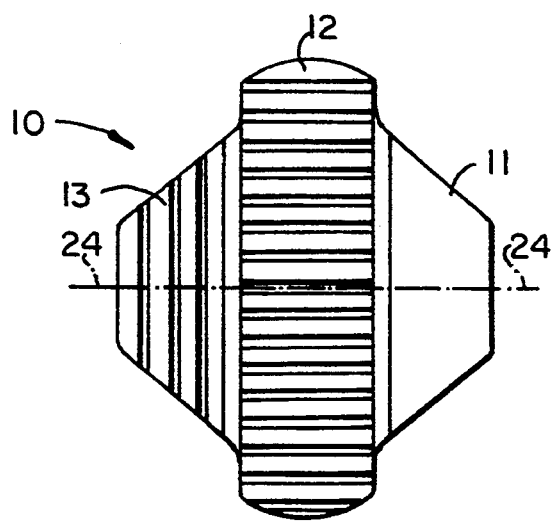
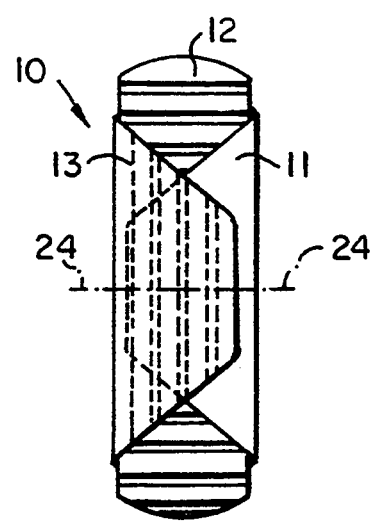
FIG.5a　　　FIG.5b
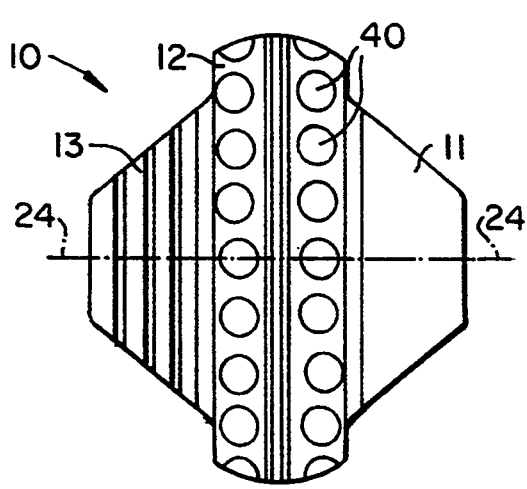
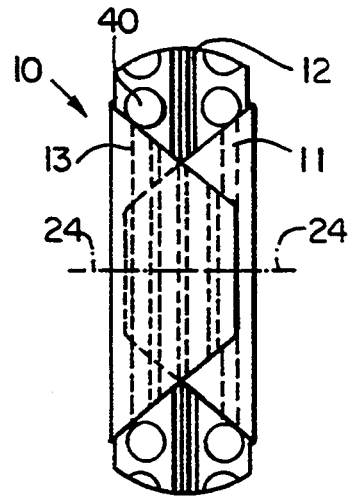
FIG.6a　　　FIG.6b
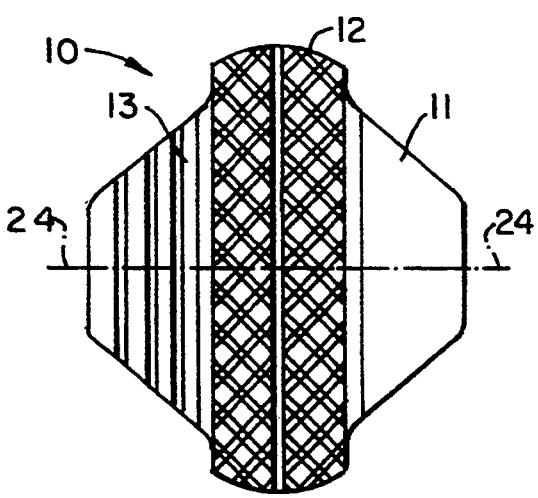
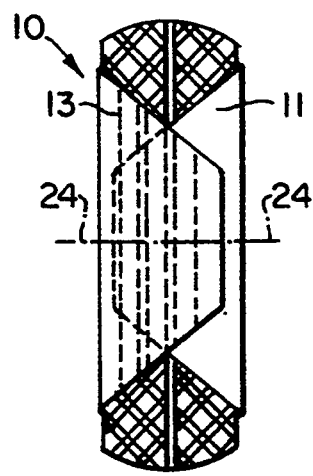
FIG.7a　　　FIG.7b

STABILIZED ABSORBENT CORE AND PRODUCTS MADE THEREFROM

FIELD OF THE INVENTION

This invention relates to absorbent materials useful in the manufacture of absorbent products, such as sanitary napkins, and to such absorbent products.

BACKGROUND OF THE INVENTION

Despite the many advances that have been made in the design of absorbent products such as diapers, incontinent products and sanitary napkins, there is a constant need for improved products that will offer the user greater security. Ways to enhance the absorbent capacity of such products have been found and widely utilized, for example, the inclusion of superabsorbent materials in product design. However, despite increased absorbent capacity, tests show that a surprisingly high proportion of such products still fail, i.e., the wearer experiences leakage and staining. In large part, such failure is due to the stress imposed upon the product during use. A sanitary napkin, for example, is subjected to significant distortional forces by the wearer's body movements. These forces can tend to compress the napkin laterally, causing it to rope or twist and thereby present a smaller area for fluid pick-up. Although this problem has been addressed in the art, there remains a need for new product designs that will successfully alleviate such distortion problems but that are also easily manufactured so that cost-effective products can be offered to consumers.

A number of patents have published disclosing sanitary napkins having an absorbent batt folded in a particular configuration.

U.S. Pat. No. 4,576,596 to Jackson et al. discloses a napkin in which an absorbent batt is folded on itself at least on each longitudinal axis with the fold being maintained by fusing areas of the adjacent layers over the batt near the folded edge.

U.K. Patent Application GB 2,124,499A discloses a sanitary napkin with an absorbent batt folded along the longitudinal edges to provide a cavity in the bottom portion of the napkin.

U.S. Pat. No. 3,699,966 to Chapuis discloses a sanitary napkin comprising alternate layers of hydrophilic and hydrophobic material, with the edges of the hydrophilic material folded inward to define a channel extending through the middle of one side of the napkin.

Other patents disclosing napkins containing an absorbent batt folded in a "C-fold" configuration are U.S. Pat. No. 3,667,468 to Nystrand et al., U.S. Pat. No. 3,954,107 to Chesky et al., and U.S. Pat. No. 3,364,931 to Hirsch.

SUMMARY OF THE INVENTION

This invention relates to an absorbent product for use in a wearer's garment, such as a sanitary napkin, comprising
a body-facing, fluid-pervious cover,
a garment-facing, fluid-impervious backing, and
an absorbent batt therebetween, said absorbent batt being folded upon itself along a pair of generally parallel longitudinal fold lines to form a middle panel and two side panels said middle and two side panels being substantially equivalent in width at the central transverse axis of said absorbent batt. The middle panel is preferably positioned on the body-facing side of the absorbent batt.

In preferred embodiments, one or more panels of the absorbent batt are pattern-embossed to effect fluid acquisition, holding and transport in the product. For example, in one preferred embodiment, the body-facing panel is provided with a plurality of lengthwise channels and one of the side panels is provided with a plurality of widthwise channels, such channels serving to wick fluid away from the center of the absorbent batt.

The absorbent product of the invention offers numerous advantages. The folds at the side edges of the absorbent batt provide the tri-folded absorbent batt with an inherent mechanical bending resistance which, in turn, gives the batt an enhanced ability to provide a springy force to resist deformation, collapsing or roping.

BRIEF DESCRIPTION OF THE DRAWINGS

FIGS. 5, 6, 7, 8, and 9 are top views of various absorbent batts of this invention, both prior (a) and after (b) folding.

DETAILED DESCRIPTION OF THE INVENTION

Figure 1:
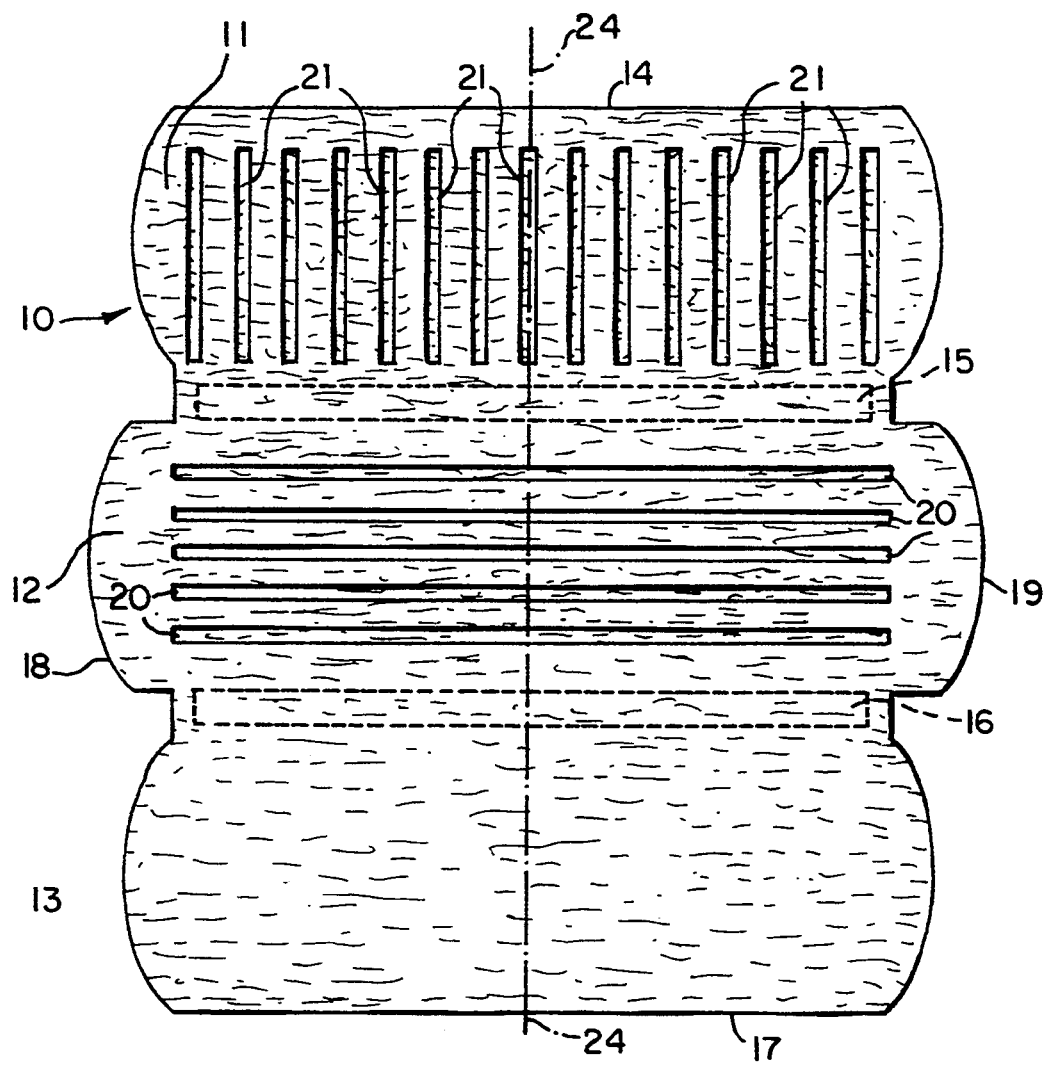
FIG. 1 is a top view of an absorbent batt of this invention, prior to being folded.

The absorbent batt utilized in this invention is illustrated in the FIGS. 1–3 and 5–9. Absorbent batt 10 comprises three panels, 11, 12 and 13. Side panel 11 is defined by longitudinal edge 14 and by longitudinal fold line 15. Middle panel 12 is defined by longitudinal fold line 15 and by longitudinal fold line 16. Side panel 13 is defined by longitudinal fold line 16 and by longitudinal edge 17. The transverse ends of each of the three panels are defined by transverse edges 18 and 19. Dotted line 24 represents the central, transverse axis of the absorbent batt, an axis located midway between transverse edges 18 and 19.

Fold lines 15 and 16 are generally parallel to one another and are positioned so that each of panels 11, 12 and 13 are substantially equivalent in width at the central transverse axis of the absorbent batt. When panels 11 and 12 are folded at fold lines 15 and 16, the absorbent batt is not in a traditional C-fold configuration. Rather, there is a substantial overlap of side panel 11 and middle panel 12. By substantial overlap it is meant that side panel 11 is folded over middle panel 12 so that longitudinal edge 14 approaches fold line 16 at central transverse axis 24 while still permitting folding about line 16 as shown in the figures. Similarly, side panel 13 is folded over the opposite face 22 of side panel 11 so that longitudinal edge 17 approaches the fold formed at fold line 15 at the central transverse axis 24.

As shown in FIG. 1, the panels 11, 12 and 13 can be substantially equivalent in width through their entire length. Alternatively, however, as shown in FIGS. 5, 6, 7, and 8, the three panels may be substantially equivalent in width at the central transverse axis 24, but either side panel 11 or 13 or both can taper to a narrower width as they extend longitudinally from the central transverse axis in a variety of patterns. By altering the shapes of side panels 11 and/or 13, it is possible to provide an absorbent batt that is thicker in the central region, where greater absorbency is required, and thinner at the end regions where less absorbency is required, the thinner end regions contributing to greater comfort for the wearer. For example, as shown in FIGS. 5, 6, 7 and 8, side panels 11 and 13 may be generally trapezoidal in shape.

The three panels 11, 12 and 13 may be substantially equivalent in length, as shown in FIG. 1, or their lengths may vary. For example, in the embodiments illustrated in FIG. 9, each of side panels 11 and 13 is shorter in length than middle panel 12. This configuration, too, provides for a pad that is thicker in the central region than at the longitudinal ends, providing both increased comfort and increased absorbency where needed.

The absorbent batt is preferably formed from both absorbent pulp fibers and resilient, synthetic fibers. The pulp fibers are generally formed from fiberizing wood pulp sheets and generally comprise a combination of long and short fibers. Suitable resilient, synthetic fibers include, but are not limited to, polyester and polyethylene fibers. These fibers tend to be "long", i.e., in the range of about 1/16" to about ½" long. While the pulp fibers imbue the batt with absorbency, the synthetic fibers add to the resiliency of the batt.

The relative amounts of pulp fibers and synthetic fibers are not critical and can be determined by one skilled in designing such products, in an effort to balance and achieve the desired properties of absorbency and resiliency. Generally, however, the synthetic fibers will comprise between about 10% and about 40% of the total fibers in the absorbent batt.

The wood pulp fibers and synthetic fibers may be blended homogeneously throughout the batt, or the relative proportions of each may vary throughout the batt. For example, it may be desirable to have a greater proportion of pulp fibers to synthetic fibers in the body-facing panel of the absorbent batt, panel 12, to enhance the ability of that panel to quickly absorb fluid, and a lower proportion of pulp fibers to synthetic fibers in the garment-facing panel of the absorbent batt, panel 13, where rapid fluid pick-up is not as critical but where added resiliency is beneficial.

The relative quantities of fibers in each panel can range from 100% to 0% pulp to 0% to 100% synthetic fiber. When middle panel 12 is on the body-facing side of the batt, it is desirable to have rapid fluid distribution in that panel, so middle panel may be beneficially formed from 100% pulp. In side panels 11 and 13, where rapid fluid absorption is not as critical, 100% synthetic fiber can be utilized for resiliency. For process simplicity, however, it is generally desirable to have a uniform blend of fibers throughout the three panels. A composite of about 65% pulp and 35% synthetic fiber has been found to provide an absorbent batt with good resiliency.

The resiliency of the batt can vary greatly with the type and length of the synthetic fibers utilized. Since the length and resiliency of most synthetic fiber decreases after it is heated to above its melt temperature, it is desirable to use a short ($<1/16''$) synthetic fiber with a low melt temperature in conjunction with a long synthetic fiber with a high melt temperature. The shorter and lower melt fiber is used to bond the pulp and synthetic fibers together and the longer and higher melt fiber can provide the resilient property that is desired. For example, a batt with a composite of 65% pulp, 20% short low melt synthetic fiber and 15% longer high melt synthetic fiber (a total of 35% synthetic fiber) provides an absorbent batt with better resiliency than a standard 65/35 composite.

The batt may be formed by known techniques in which the fibers, pulp and/or synthetic, are airlaid. To form the most stable batt, the fibers in the batt are preferably bonded to one another. This may be done by heating the batt to a temperature above the melting temperature of the synthetic fibers so those fibers fuse and bond to one another. Alternatively, bonding agents such as different thermo-bonding fibers, hot melt spray adhesives, and bonding powders may be utilized. Specific means that can be used to bond the fibers together include convection ovens, di-electric ovens (radio frequency and microwave), infrared ovens, heated calender rolls, forced hot-air ovens, forced hot air during the panel forming process, and spray hot melt adhesive during the panel forming process.

The figures illustrate a tri-fold configuration of the absorbent batt. It is believed that the folded edges formed at fold lines 15 and 16 provide the absorbent batt with resistance to bending forces. This gives the batt the ability to provide a springy force to resist deformation, collapsing or "roping" when subjected to lateral crushing forces, such as those provided to the lateral edges of a sanitary napkin by movement of the wearer's thighs.

Any one of, or all of, panels 11, 12 and 13 may be provided with embossing to enhance fluid distribution, comfort and/or aesthetics. Such embossing patterns can include, but are not limited to, lengthwise or widthwise channels, diagonal channels, and pockets of embossing.

In one embodiment illustrated in FIG. 1, middle panel 12 has a plurality of longitudinal channels formed therein, and side panel 11 has a plurality of widthwise channels formed therein. In another embodiment, illustrated in FIG. 5, side panel 13 has a plurality of longitudinal channels and middle panel 12 has a plurality of widthwise channels. FIG. 7 shows side panel 13 having a plurality of longitudinal channels and middle panel 12 having a plurality of diagonal channels. The channels provided in the various panels of the absorbent batt serve to wick fluid to all portions of the absorbent batt.

In the embodiment illustrated in FIG. 6, side panel 11 is provided with longitudinal channels and middle panel 12 has been embossed to provide a plurality of raised circular areas 40 on the panel. The raised circular areas provide a feeling of loft and softness, and the indentations around those areas provide a reservoir for acquisition of fluid.

The embossing patterns provided on the absorbent panels may be provided by means known in the art, for example, by a patterned calender roll, which may or may not be heated. The pitch/pattern for the channel embossing can vary within each respective tooling roll and vary from one pattern to another. An embossing station may be designed to house an upper and lower calender roll which can be set up in a male to female orientation or male to a solid anvil. The rolls can be heated or maintained at ambient temperature depending on the composition of the batt and the desired "set" that is required for specific products. In general, a permanent set can be made on a batt with pulp content of between 65% to 100% without the use of heat. A small amount of moisture, 0.5% to 5% of the weight of the batt, can be added to the batt containing a percentage of pull to obtain a stronger and more permanent set. Batts with a lower percentage of pulp may require heat to obtain a permanent set.

The pulp pad can be processed through the embossing station with the depth of embossing determined by the pulp thickness and composition. For example, the specification for longitudinal or latitudinal rolls might be as follows: Rolls 1″–2″ wide with varying channel pattern of $\frac{1}{8}″$–$\frac{1}{2}″$ male, $\frac{1}{8}″$–$\frac{1}{2}″$ female with a depth of $\frac{1}{8}″$ to $\frac{1}{4}″$, angle of 60° to 90°. Preferably, the densified channels or areas are at least $\frac{1}{4}″$ from the edges and ends of the panel.

Figure 2:
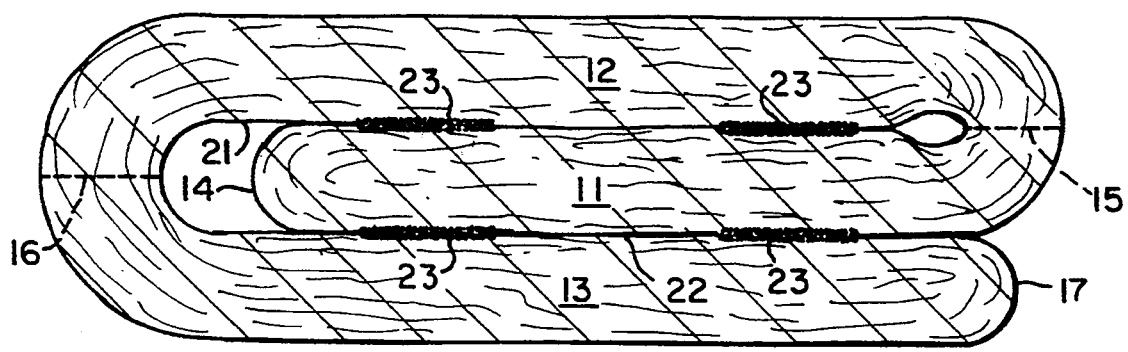
FIGS. 2 and 3 are cross-sections of tri-folded absorbent batts utilized in this invention.
Figure 3:
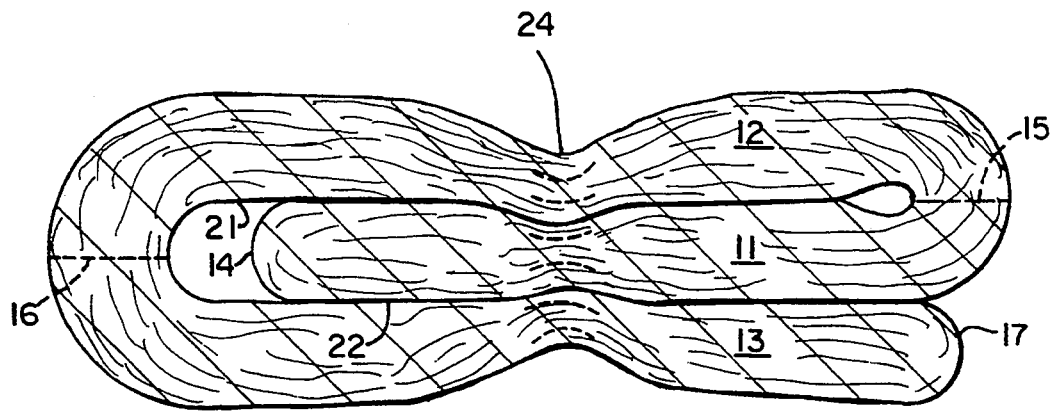

Preferably, the panels of the tri-folded absorbent batt 10 are bonded to one another to help retain the tri-folded configuration. This may be done by application of areas of construction adhesive 23, as illustrated in FIG. 2. Alternatively, the tri-folded panel may be subjected to heat and/or calendaring to effect bonding of the panels through bonding of the thermoplastic fibers therein, as illustrated in FIG. 3.

Additional fibrous or particulate agents may be incorporated into the fibrous batt. For example, it may be desirable to incorporate superabsorbent particles or fibers in the batt to enhance the absorbency of the batt. Such superabsorbents are well known in the art. One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides including, for example, cellulose and starch and regenerated cellulose which are modified by being carboxylalkylated, phosphonoalkylated, sulfoalkylated, or phosphorylated to render them highly hydrophilic. Such modified polymers may also be cross-linked to improve their water-insolubility.

It may also be desirable to incorporate odor control agents in the batt, such as but not limited to, baking soda and activated charcoal.

Figure 4:
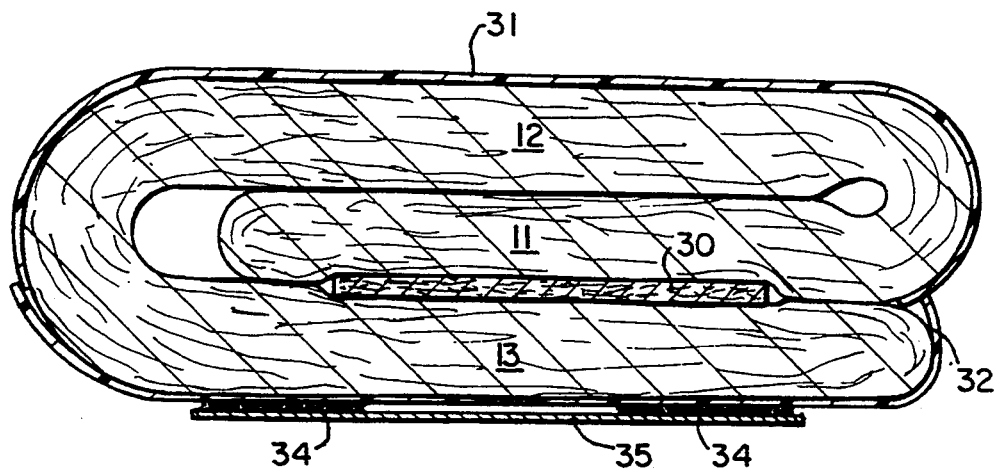
FIG. 4 is a cross-section of a sanitary napkin incorporating the tri-folded absorbent batt.
Figure 8A:
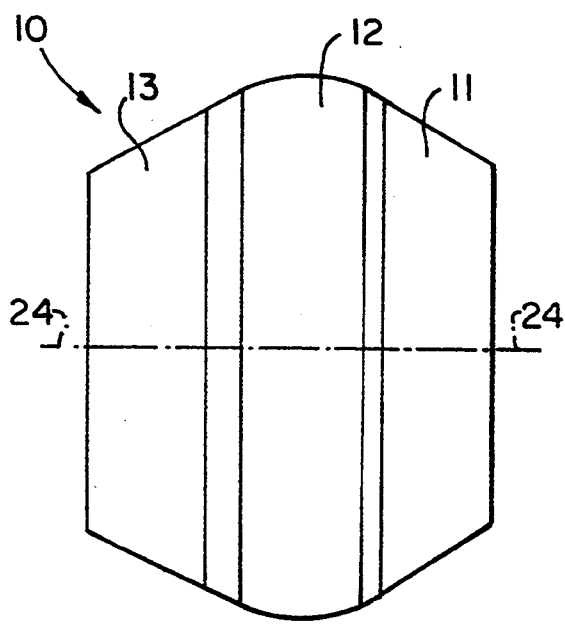
Figure 8B:
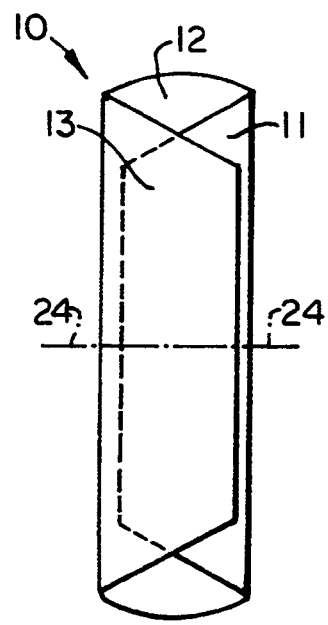
Figure 9A:
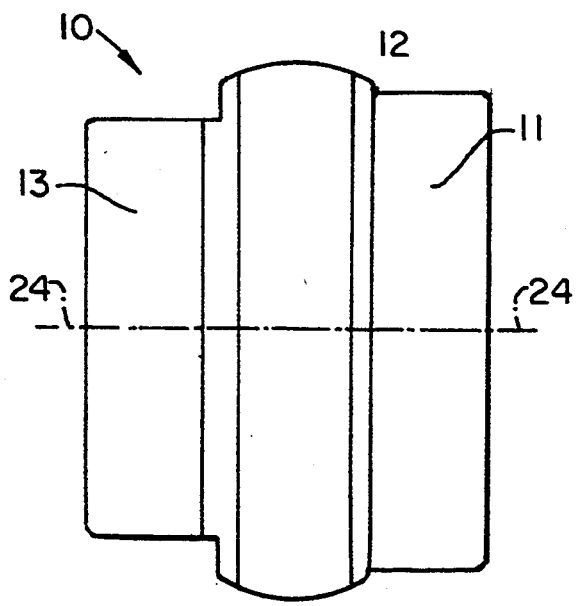
Figure 9B:
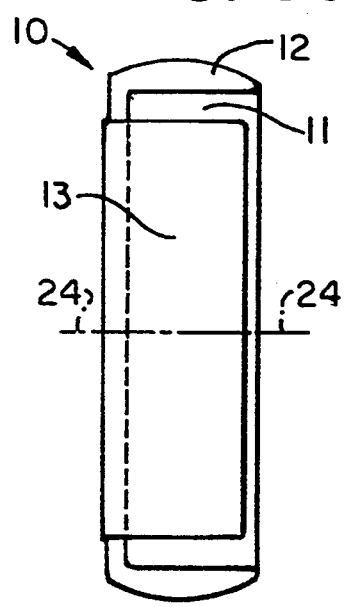

Rather than incorporating superabsorbent or odor control agents within the batt itself, these materials may be placed or layered between the panels of the tri-folded batt. For example, baking soda powder or fibrous or particulate superabsorbent may be placed on the surface of the absorbent batt prior to folding, so that it is positioned between the layered panels in the final configuration of the batt. As another example, a panel of superabsorbent material, for example a superabsorbent/tissue laminate or a panel of processed peat moss, either of which may be represented by insert 30 as shown on FIG. 4, may be placed between panels of the tri-folded batt As illustrated in the figures, each of the three panels in the absorbent batt is generally uniform in thickness. However, the thickness of the panels can vary to provide different profiles. For example, it may be desired to have extra thickness in the center of the napkin, so the thickness of one or more of the panels could be greater in the center than at either or both the transverse or longitudinal edges.

The dimensions of the absorbent batt are not critical and can be varied according to the type of absorbent product desired. Generally, for a full protection sanitary napkin, the absorbent batt might be in the range of about 8″ in length and about 7″ in width, before tri-folding.

A sanitary napkin incorporating the tri-folded absorbent batt described above is illustrated in FIG. 4. The absorbent batt is contained within a top body-facing, fluid-pervious cover 31 and a bottom, garment-facing, fluid-impervious backing 32. Adhesive means 34 serve to securely adhere the napkin to the wearer's undergarment. The attachment means may comprise adhesive lines covered with release strips 35 which, when peeled from the adhesive strips, leave the adhesive tacky. Alternatively, the attachment means may comprise pressure-sensitive adhesive tape, said tape having a first face permanently adhered to the liquid impermeable cover 32 and an opposite second face adapted to be temporarily attached to the wearer's garment.

The absorbent batt is preferably placed in the napkin so that middle panel 12, having longitudinal channels, is the body-facing side of the batt and so that side panel 11, having widthwise channels, is the middle portion of the batt.

The fluid-pervious cover 31 facing provided on the absorbent structure of the present invention should be a film or fabric having a high degree of moisture permeability. For example, the fabric may be polyester, polyethylene, polypropylene, bicomponent fiber, nylon, rayon, or the like. The most suitable fabrics have unusually high elongation, loft, softness and drape characteristics. Films which are perforated or noncontinuous are also satisfactory. Though the cover is moisture permeable, it is preferably of the type which after permeation of the moisture, prevents strike-back of the body fluid when the absorbent structure is approaching saturation.

The fluid-impervious backing 32 may be a liquid-impermeable polyolefin film, e.g., polyethylene or polyethylene terephthalate.

What is claimed is:

1. An absorbent product for use in a wearer's garment comprising
    a body-facing, fluid-pervious cover,
    a garment-facing, fluid-impervious backing,
    an absorbent batt therebetween, said absorbent batt being folded upon itself along a pair of generally parallel longitudinal fold lines to form a middle panel and two side panels, said three panels being substantially equivalent in width at the central transverse axis of said absorbent batt; wherein said middle panel is on the body-facing side of said absorbent batt, and wherein said absorbent batt comprises wood pulp fibers and synthetic fibers such that the proportion of wood pulp fibers to synthetic fibers is greater in said middle, body-facing panel of said absorbent batt than in said side panels, and said absorbent batt comprises wood pulp fibers and synthetic fibers such that the proportion of synthetic fibers to wood pulp fibers is greater in said side panels.

2. An absorbent product of claim 1 which is a sanitary napkin.

3. An absorbent product of claim 1 wherein said middle body-facing panel is bonded to a first side panel and said first side panel is bonded to a second side panel.

4. An absorbent product of claim 1 wherein superabsorbent material is placed between said middle body-facing panel and one of said side panels of said absorbent batt.

5. An absorbent product of claim 1 wherein odor-controlling material is placed between said middle body-facing panel and one of said side panels of said absorbent batt.

6. An absorbent product of claim 1 wherein at least one of said side panels is shorter in length than said middle, body-facing panel.

7. The absorbent product of claim 1 wherein said middle panel comprises the proportion of about 65% wood pulp to about 35% synthetic fiber.

8. The absorbent product of claim 1 wherein said middle panel comprises the proportion of about 65% wood pulp to about 35% synthetic polymer and said side panels each comprise the proportion of 0% wood pulp to 100% synthetic fiber.

9. The absorbent product of claim 1 wherein the synthetic fiber comprises about 10% to about 40% of the total fiber in the absorbent batt.

10. An absorbent product of claim 1 wherein said side panels of said absorbent batt are narrower in width at their transverse ends than at the central transverse axis of the absorbent batt.

11. An absorbent product of claim 10 wherein said side panels are generally trapezoidal in shape.

12. An absorbent product of claim 1 wherein one or more panels of said absorbent batt is pattern-embossed.

13. An absorbent product of claim 6 wherein said pattern is selected from the group consisting of longitudinal channels, latitudinal channels, diagonal channels and raised dots.

14. An absorbent product for use in a wearer's garment comprising
   a body-facing, fluid-pervious cover,
   a garment-facing, fluid-impervious backing,
   a tri-folded absorbent batt therebetween, wherein said absorbent batt comprises
      a first panel defined by a first longitudinal edge of said batt and a first longitudinal fold line, said first panel having a plurality of widthwise channels,
      a second panel defined by said first longitudinal fold line and a second longitudinal fold line, said second panel having a plurality of lengthwise channels,
      a third panel defined by said second longitudinal fold line and a second longitudinal edge of said batt,
and wherein said first panel is folded over one face of said second panel at said first fold line so there is a substantial overlap of said first and second panels, and where said third panel is folded over said first panel at said second fold line; said second panel thereby is on the body-facing side of said absorbent batt; wherein said absorbent batt comprises wood pulp fibers and synthetic fibers such that the proportion of wood pulp fibers to synthetic fibers is greater in said second body-facing panel of said absorbent batt than in said first and third panels, and said absorbent batt comprises wood pulp fibers and synthetic fibers such that the proportion of synthetic fibers to wood pulp fibers is greater in said first and third panels.

15. The absorbent product of claim 14 wherein said second panel comprises the proportion of about 65% wood pulp to about 35% synthetic fiber.

16. The absorbent product of claim 14 wherein said second panel comprises the proportion of about 65% wood pulp to about 35% synthetic polymer and said first and third panels each comprise the proportion of 0% wood pulp to 100% synthetic fiber.

17. The absorbent product of claim 14 wherein the synthetic fiber comprises about 10% to about 40% of the total fiber in the absorbent batt.

18. An absorbent core for use in an absorbent product suitable for placement in a wearer's garment comprising an absorbent batt folded upon itself along a pair of generally parallel longitudinal fold lines to form a middle panel and two side panels, said three panels being substantially equivalent in width at the central transverse axis of said absorbent batt; wherein said absorbent batt comprises wood pulp fibers and synthetic fibers such that the proportion of wood pulp fibers to synthetic fibers is greater in said middle panel of said absorbent batt than in said side panels, and said absorbent batt comprises wood pulp fibers and synthetic fibers such that the proportion of synthetic fibers to wood pulp fibers is greater in said side panels.

19. An absorbent core of claim 18 wherein said middle panel is bonded to one of said side panel and said side panel is bonded to said other side panel.

20. An absorbent core of claim 18 wherein superabsorbent material is placed between said middle panel and one of said side panel of said absorbent batt.

21. An absorbent core of claim 18 wherein odor-controlling material is placed between said middle panel and one of said side panel of said absorbent batt.

22. An absorbent core of claim 18 wherein at least one of said side panels is shorter in length than said middle panel.

23. The absorbent product of claim 18 wherein said middle panel comprises the proportion of about 65% wood pulp to about 35% synthetic fiber.

24. The absorbent product of claim 18 wherein said middle panel comprises the proportion of about 65% wood pulp to about 35% synthetic fiber and said side panels each comprise the proportion of 0% wood pulp to 100% synthetic fiber.

25. The absorbent product of claim 20 wherein the synthetic fiber comprises about 10% to about 40% of the total fiber in the absorbent batt.

26. An absorbent core of claim 18 wherein said side panels of said absorbent batt are narrower in width at their transverse ends than at the central transverse axis of the absorbent batt.

27. An absorbent core of claim 26 wherein said side panels are generally trapezoidal in shape.

28. An absorbent core of claim 18 wherein one or more panels of said absorbent batt is pattern-embossed.

29. An absorbent product of claim 28 wherein said patterns are selected from the group consisting of longitudinal channels, latitudinal channels, diagonal channels and raised dots.

* * * * *